United States Patent [19]  [11] 4,106,990
Karges et al. [45] Aug. 15, 1978

[54] QUANTITATIVE DETERMINATION OF ANTITHROMBIN III

[75] Inventors: Hermann Erich Karges; Norbert Heimburger, both of Marburg, Lahn, Fed. Rep. of Germany

[73] Assignee: Behringwerke Aktiengesellschaft, Marburg, Lahn, Fed. Rep. of Germany

[21] Appl. No.: 694,815

[22] Filed: Jun. 10, 1976

[30] Foreign Application Priority Data

Jan. 15, 1976 [DE] Fed. Rep. of Germany ....... 2601372

[51] Int. Cl.² .................. G01N 31/14; C07G 7/02
[52] U.S. Cl. .................... 195/63; 195/66 B; 195/103.5 R
[58] Field of Search ............. 195/63, 99, 103.5 R, 195/66 B

[56] References Cited

U.S. PATENT DOCUMENTS

| 3,497,319 | 2/1970 | Altschul | 195/103.5 R |
| 3,853,710 | 12/1974 | Innerfield | 195/103.5 R |
| 3,985,618 | 10/1976 | Innerfield | 195/103.5 R |

OTHER PUBLICATIONS

Biggs, et al., Antithrombin III, Antifactor Xa, and Heparin, Chemical Abstracts, vol. 74, 1971.

Primary Examiner—David M. Naff
Attorney, Agent, or Firm—Curtis, Morris & Safford

[57] ABSTRACT

Antithrombin III in plasma or serum is determined by combining diluted plasma or serum with heparin or heparinoids and thrombin to form a mixture, permitting the mixture to stand, thereafter adding to the mixture a fibrinogen solution and determining the coagulation time. The heparin or heparinoids and thrombin can be combined together to form a reagent for use in the determination.

3 Claims, No Drawings

QUANTITATIVE DETERMINATION OF ANTITHROMBIN III

The invention relates to a process for the quantitative determination of the antithrombin-III activity of aqueous solutions, in particular in body fluids such as plasma or serum, involving complex formation with heparin by determination of the coagulation time.

In the series of antithrombins, which have been characterized by the numbers I to VI, the antithrombin III (AT III) plays an important role. It was prepared in pure form and characterized as an $\alpha_2$-globulin having a molecular weight of 65000.

Its biological action as an inhibitor is not limited to thrombin, but it inhibits to a particular degree also factor X and the other serine-proteases from the series of coagulation factors, and also plasmin.

The interaction of the inhibitor with enzymes proceeds slowly in a time-depending reaction and, therefore, AT III is designated as a progressive inhibitor. The speed of this interaction between enzyme and inhibitor is accelerated by heparin, whereby the progressive inhibitor AT III changes its character and becomes an instantaneous inhibitor.

Owing to its central position in the coagulation and fibrinolysis system and by reason of the possibility of increasing its reaction speed with heparin, AT III has a great importance in the control of blood coagulation. Relatively small reductions of the AT III content lead to a considerable increase of thrombosis risk. In view of the corelation between thrombosis risk and the content of AT III of the blood, the determination of the AT III has found increasing interest in the last years and, besides the immunological determination methods, a series of functional tests has been developed. Most of the biological tests are carried out by incubating thrombin with the test plasma for a certain period of time and determining the activity of the thrombin after the incubation with the aid of a calibrating graph. In many determination instructions, this method requires defibrination of the plasma owing to the antithrombin I-action to the fibrin, which is carried out in many cases by heating to 56° C or with the aid of a fibrin-forming enzyme from snake venon, which is not inhibited by AT III (for example, reptilase). According to experience, the step of defibrination leads to great uncertainties in the determination and is a time-consuming measure. Moreover, the determination does not allow a differentiation between AT III and the other progressive thrombin inhibitors known in the literature.

Now, we have found that there are conditions under which the AT III activity in various media such as plasma, serum, other body fluids can be determined, without fibrinogen, $\alpha_2$-macroglobulin and $\alpha_1$-antitrypsin disturbing the determination.

Thus, the object of the invention is a process for the determination of AT III in its aqueous solutions, which comprises mixing dilute solutions of AT III, sulfated polymer and thrombin and, after addition to a fibrinogen solution, determining the coagulation time. Disturbance of the determination by the above-mentioned substances is avoided by pre-diluting, for example in the case of plasma or serum, the sample on which the determination has to be effected, at a ratio of at least 1 : 50. Such a predilution is possible, since the AT III of the sample tested is converted by sulfated organic polymers having heparin action, for example, the sodium slat of polyethylenesulfonic acids with molecular weights of several thousands, preferably heparin, from a progressive inhibitor into an instantaneous inhibitor.

The conversion of AT III into the instantaneous inhibitor may be effected in a large range of concentration with the sulfated polymers. 10 - 500 IU, preferably 25 IU, of heparin or heparinoid may be added for 1 unit of AT III (activity of 1 ml of normal plasma). A higher excess of heparin or of corresponding amounts of the sulfated polymers has a detrimental effect on the result of the determination.

The process is carried out as follows: the mixture of, for example, 2 parts by volume of diluted test specimen and 1 part by volume of sulfated polymer or heparin solution having about 0.4 - 20 IU, preferably 1 IU, is combined with 1 part by volume of a thrombin solution having an activity of 1 - 40 NIH-units, preferably 5 - 10 NIH-units. After incubation of this mixture at a defined temperature in the range of from about 4° C to 45° C, preferably 37° C, over a period of time of 2 to 20 minutes, preferably 4 minutes, an aliquot part of the incubation batch is pipetted to a standardized fibrinogen solution of about 0.05 to 1% (g/v), preferably 0.4%, and the coagulation time is then measured.

According to the invention, the determination is simplified by combining the thrombin and the polymer reacting with AT III (for example, sodium salt of polyethylenesulfonic acid or heparin) to form an AT III reagent which is optionally lyophilized.

Thus, further objects of the invention are also means for the determination of antithrombin III in its aqueous solutions, which contain a sulfated organic polymer with heparin action and thrombin in a suitable composition.

In a preferred embodiment of the process for the determination of AT III, given here as an Example, at first, for example, plasma is predicted with a solution of an alkaline buffer having a pH-value of about 7.5 to 10, preferably 0.1 M trishydroxymethylaminomethane buffer of pH 8.0 containing 0.025 M NaCl, at a ratio of 1:25 to 1:400, preferably 1:100. Then, 1 part of the diluted sample is mixed with 1 part of AT III reagent. The AT III reagent consists of a mixture of 0.2 - 10 IU of sulfated organic polymer, preferably 1 IU of heparin, and 0.5 to 20 NIH-units, preferably 10 NIH-units of thrombin in a solution of a gelatin derivative cross-linked with diisocyanate, which is commercially available under the Trade Mark Haemaccel, and which had been diluted at a ratio of 1:2 with a physiological salt solution that has no influence on the coagulation. The batch is incubated for 4 minutes at 37° C and the coagulation time is determined with an aliquote part of the incubation mixture on a standardized fibrinogen solution.

With a thrombin reference curve, it can be determined how much thrombin has been inhibited by the sample. By comparison with a reference, for example standard human plasma, it can be determined how many units or % of the standard AT III are contained in the sample, 100% of the standard of activity of 1 ml of a mixture of samples of the citrate plasma of at least 10 healthy normal persons.

The activity can also be determined with the aid of a standard regression curve for AT III.

The described AT III determination permits a reproducible, simple and rapid determination of the AT III of a sample. It is not disturbed by other antithrombins such as $\alpha_2$-macroglobulin $\alpha_1$-antitrypsin, yields a straight regression curve and corresponds well with the immunological determination of AT III.

Preparation of the thrombin calibrating curve

A thrombin solution was pre-diluted to 6 NIH-units. Starting from this dilution, there were prepared, by addition of buffer, solutions having thrombin activities of 5, 4, 3, 2 and 1 NIH-units. The coagulation times of these solutions in admixture with a standardized fibrinogen solution (0.4% ml of fibrinogen in Tris buffer pH 8.0), 0.2 ml of fibrinogen solution and 0.1 ml of thrombin solution, were determined. The coagulation times (ordinate) were plotted on double logarithmic paper against the units of thrombin (abscissa). On a thrombin calibrating curve the residual activities of thrombin in the incubation batches can be determined by recording the coagulation times.

Thrombin calibrating curve
Units of thrombin; Coagulation time
6 NIH-U; 31.1 sec.
5 NIH-U; 35.5 sec.
5 NIH-U; 41.3 sec.
3 NIH-U; 51.6 sec.
2 NIH-U; 70.7 sec.
1 NIH-U; 105.4 sec.

EXAMPLE

Determination of the AT III content in a serum or plasma sample

The determination is effected in three steps: 1. Predilution

The sample is pre-diluted with 0.1 M Tris-buffer of pH 8.0, which contains 0.025 M NaCl, in two steps in a ratio of 1:100 (for example, 1. step: 0.1 ml of sample + 0.9 ml of buffer; 2. step: 0.1 ml of the sample diluted at 1:10 + 0.9 ml of buffer). 2. Incubation 0.2 ml of the sample diluted at 1:100 from step 1 is mixed with 0.2 ml of AT III reagent and incubated for 4 minutes at 37° C.

3. Coagulation 0.2 ml of a fibrinogen solution standardized to 0.4% by weight is mixed with 0.1 ml of the incubation mixture of step 2, and the coagulation time is determined at 37° C.

The residual activity of thrombin in the incubation batch corresponding to the coagulation time is then read from the thrombin calibration curve, from which it can be calculated according to the following formula $$T = T_v - T_a,$$

in which $T$ represents the number of inhibited units of thrombin in the sample, $T_v$ represents the number of the units of thrombin used in the incubation batch and $T_a$ represents the number of thrombin units found after the incubation, how many units of thrombin are inhibited by the sample. Upon comparison with a reference, the quantity of AT III in the sample can be calculated according to the simple formula:

$$G = (T/T_s) \cdot G_s,$$

in which $G$ represents the content of AT III in the sample, $T_s$ represents the number of inhibited units of thrombine of a reference solution and $G_s$ represents the content of AT III of the reference solution.

We claim:
1. A method for quantitatively determining antithrombin III in plasma or serum, which method comprises combining
   (a) 1 ml of said plasma or serum, diluted by at least 1 to 50,
   (b) 0.2 to 10 IU of a sulfated organic polymer selected from the group consisting of heparin and heparinoids, and
   (c) 0.5 to 20 NIH units of thrombin, at a temperature of 4° C to 45° C, permitting the mixture to stand for 2 to 20 minutes, thereafter combining one part by volume of the mixture with one part by volume of a 0.05 to 1 percent solution of fibrinogen, and determining the coagulation time of the resultant mixture.

2. A reagent for the quantitative determination of antithrombin III in plasma or serum, said reagent consisting essentially of 0.2 to 10 IU of a sulfated organic polymer selected from the group consisting of heparin and heparinoids, and 0.5 to 2 NIH units of thrombin.

3. A reagent as in claim 2 in lyophilized form.

* * * * *